United States Patent [19]
Cullinan

[11] Patent Number: 6,107,346
[45] Date of Patent: Aug. 22, 2000

[54] METHODS FOR TREATING HYPERLIPIDEMIA

[75] Inventor: George Joseph Cullinan, Trafalgar, Ind.

[73] Assignee: Eli Lilly and Company, Indianapolis, Ind.

[21] Appl. No.: 09/128,875

[22] Filed: Aug. 4, 1998

Related U.S. Application Data

[60] Provisional application No. 60/055,365, Aug. 11, 1997.

[51] Int. Cl.[7] .................................................. A61K 31/12
[52] U.S. Cl. ........................ 514/686; 514/680; 514/684; 514/824; 514/874
[58] Field of Search ...................... 514/680, 684, 514/686, 824, 874; 568/326, 329, 330, 333

[56] References Cited

U.S. PATENT DOCUMENTS

| | | | |
|---|---|---|---|
| 3,274,213 | 9/1966 | Lednicer | 260/326.5 |
| 4,017,546 | 4/1977 | Suarez et al. | 260/591 |
| 4,230,862 | 10/1980 | Suarez et al. | 546/237 |
| 4,302,435 | 11/1981 | Gosser | 423/591 |
| 5,395,842 | 3/1995 | Labrie et al. | 514/320 |
| 5,446,061 | 8/1995 | Bryant et al. | 514/456 |
| 5,484,795 | 1/1996 | Bryant et al. | 514/319 |
| 5,552,412 | 9/1996 | Cameron et al. | 514/317 |
| 5,567,712 | 10/1996 | Palkowitz | 514/231.2 |
| 5,574,190 | 11/1996 | Palkowitz | 568/440 |

FOREIGN PATENT DOCUMENTS

| | | |
|---|---|---|
| 729 951 A1 | 2/1996 | European Pat. Off. . |
| WO 95/10513 | 4/1995 | WIPO . |
| WO 96/21656 | 7/1996 | WIPO . |

OTHER PUBLICATIONS

Crenshaw, R.R., et al., Potential Antifertility Agents, *J. Med. Chem.* vol. 14, No. 12, pp. 1185–1190 (1971).

Jones, C.D., et al., Antiestrogens, *J. Med. Chem.* vol. 27, pp. 1057–1066 (1984).

Jones, C.D., et al., Antiestrogens, *J. Med. Chem.* vol. 35, pp. 931–938 (1992).

Silvestri et al, Antifungal agents; Farmaco, 50(4), pp. 227–238, 1995.

*Primary Examiner*—Sreeni Padmanabhan
*Attorney, Agent, or Firm*—Scott Alexander McNeil; James J. Sales

[57] ABSTRACT

The present application relates to a series of compounds, and pharmaceutical formulations thereof, of the formula

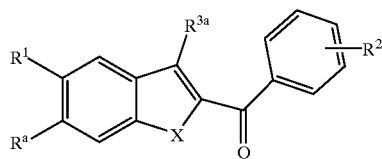

which provide a method of inhibiting hyperlipidemia, especially hypercholesterolemia, and the pathological sequelae thereof, in mammals, including humans.

11 Claims, No Drawings

METHODS FOR TREATING HYPERLIPIDEMIA

This application claims the benefit of U.S. Provisional application Ser. No. 60/055,365, filed Aug. 11, 1997.

FIELD OF THE INVENTION

The current invention relates to the fields of medicinal organic chemistry, pharmacology, and medicine. Further, the current invention relates to a group of known and novel compounds which demonstrate the potential for treating a pathological state known as hyperlipidemia in mammals, including humans.

BACKGROUND OF THE INVENTION

Hyperlipidemia is a pathological state in mammals, where there is an abnormally high concentration of lipids circulating in the serum. The composition of the lipid pool in the circulation consists mostly of triglyceride (fatty acid esters of glycerol), cholesterol, and fatty acid esters of cholesterol. Such lipophillic molecules are poorly soluble in the aqueous environment of the serum and are, therefore, rarely found as free entities in the circulation. Such molecules are generally found bound to specific proteins in the form of complexes which act as transporting mechanisms. The specific, lipid carrying proteins are known as a class as apoproteins. Various combinations of different and specific lipids and apoproteins form particles (lipoproteins) which serve both to transport lipids and perform specific biological functions. In general, such particles are physically classified by their density, e.g., high density lipoproteins (HDL)—1.063–1.210 g/mL, low density lipoproteins (LDL)—1.019–1.063 g/mL, very low lipoproteins (VLDL)—<1.006 g/mL, etc. In addition, each of these particles contains a specific profile of lipid composition, e.g., HDL contains mostly cholesterol and its esters, whereas LDL's contain more or exclusively triglycerides.

Common pathological sequelae of hyperlipidemia, especially hypercholesterolemia, are atherosclerosis, hypertension, ischemic events, such as, myocardial infarction, cerebral stroke, and organ insufficiency and thrombosis.

A commonly used index of identifying human patients at risk of the pathological sequelae of hyperlipidemia, is the determination of total serum cholesterol. Generally, in adults, total serum cholesterol levels greater than 240 mg/dL are indicative of potential danger of hyperlipidemia, while levels <200 mg/dL are considered normal. As a rough measurement, these criteria are reasonably accurate. However, total cholesterol does not reflect the relative amounts or ratio of cholesterol in the various lipoproteins, e.g., HDL versus LDL. This ratio of the distribution of cholesterol has also been shown to correlate to the potential risk of developing cardiovascular disease due to hyperlipidemia. Thus, the total amount of cholesterol and its distribution are risk factors.

In a large and long epidemiologic study (Framingham Study), it was shown that hyperlipidemia, especially hypercholesterolemia, is a risk factor for atherosclerosis. However, this study also demonstrated that a high ratio of HDL to LDL decreases the chances of developing atherosclerosis. Therefore, in order to treat or prevent hyperlipidemia, this study suggests that it is more efficacious to both lower the total serum cholesterol and to raise the ratio of HDL to LDL than to only lower total cholesterol levels.

Many drugs are available which lower-total serum cholesterol, e.g., the chemical classes known as the statins. These agents have been useful in both treating and preventing hyperlipidemia. However, these agents have little or no effect on the ratio of HDL to LDL.

Agents or life-styles are known to effect the HDL-LDL ratio, e.g., exercise raises HDL, smoking lowers HDL, small amounts of alcohol raise HDL, and hormones may either raise or lower the ratio. Most germane, to the current invention, is the effect which estrogen has on the HDL-LDL ratio.

Premenopausal women, normally, have higher levels of HDL as than their male counterparts. Premenopausal women also have less cardiovascular disease, especially disease related to hyperlipidemia, as compared to males in the same age group. However, postmenopausal women, or women at the menopause, have an increased risk for cardiovascular disease sometimes even surpassing the risk of their male counterparts. At the menopause, women demonstrate a rapid rise in total serum cholesterol and a lowering of HDL. The exact mechanism of this change is not well understood; however, women, who receive Hormone Replacement Therapy, HRT, (estrogens and/or progestins), show a normalization of total serum cholesterol, HDL-LDL ratio, and a lessening in the risk of cardiovascular disease. Estrogen is believed to exert one of its cardiovascular protecting effects by increasing HDL levels.

Although there are many factors controlling the levels of HDL which are known, the entire control mechanism is not totally understood. One factor thought to be important in this process is the effect of hepatic lipase. Hepatic lipase, a liver enzyme, is a major factor in controlling the degradation of HDL particles. This enzyme facilitates the hydrolysis of HDL phospholipids and triglycerides and the subsequent dissolution of the lipoprotein particle. Recently, it has been found that the gene coding for this enzyme, controlled by many factors, is down-regulated by the hormone estrogen. This down-regulation of the lipase gene and subsequent lowering of the production of the enzyme, may, at least in part, explain the rise in HDL and lowering of cardiovascular risk in postmenopausal women on HRT. (For further information see: "Harrison's Principles of Internal Medicine", Eds. Iselbacher, et al., 9th Ed., McGraw-Hill Co., NYC, Chap. 250, pp. 1159–1168 and Chap.99, pp.507–518 and references therein; and Oka, K. et al., "Transcription of the human lipase gene is modulated by multiple negative elements in HepG2 cells.", Gene, 180, p.69–80 (1996) and references therein.)

Today, HRT is used in women to ameliorate the cardiovascular effects of menopause. This therapy, while effective, suffers from poor patient compliance, due to unpleasant side-effects, poor oral absorption, and poor bio-availability of the natural estrogens 17-b-estradiol and estrone.

Compounds of the current invention, i.e., the compounds of formula I(b), have the potential of down regulating the expression of hepatic lipase, thus raising the levels of HDL. This effect of raising HDL indicates usefulness in treating hyperlipidemia, especially hypercholesterolemia, and its subsequent pathological sequelae. In addition, compounds of the current invention are well absorbed by the oral route and possess favorable bio-availability properties.

SUMMARY OF THE INVENTION

The current invention relates to compounds of formula I(a):

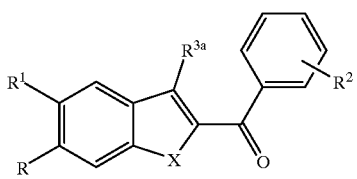

I(a)

where

R, $R^1$, and $R^2$ are independently at each occurrence hydrogen, hydroxy, or —O—Pg;

Pg is a hydroxy protecting group;

X is —$CH_2$—, —$CH_2$—$CH_2$—, or —CH=CH—;

$R^{3a}$ is hydrogen, $C_1$–$C_6$ alkyl, $C_3$–$C_6$ cycloalkyl, or a moiety of the formula (a), (b), or (c):

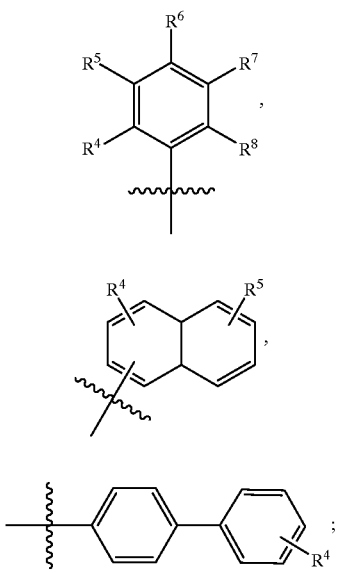

(a)

(b)

(c)

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy, with the proviso that, in the moiety of formula (a), $R^4$, $R^5$, $R^6$, $R^7$, and $R^8$ can not all be hydrogen;

or a pharmaceutically acceptable salt or solvate thereof.

Further, the current invention provides methods for inhibiting hyperlipidemia, especially hypercholesterolemia, and the pathological sequelae thereof, in mammals, including humans, which includes administering to a mammal in need thereof an effective amount of a compound of formula I(b):

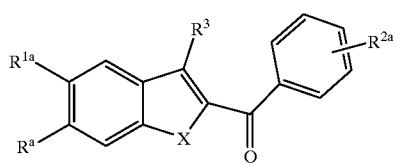

I(b)

where $R^a$, $R^{1a}$, and $R^{2a}$ are independently at each occurrence hydrogen, hydroxy, —O($C_1$–$C_4$ alkyl), —OCO($C_1$–$C_4$ alkyl), —OCOAr, —$OCO_2$($C_1$–$C_4$ alkyl), —$OCO_2$Ar, or $C_3$–$C_6$ cycloalkoxy;

Ar is phenyl or substituted phenyl;

X is —$CH_2$—, —$CH_2$—$CH_2$—, or —CH=CH—;

$R^3$ is hydrogen, $C_1$–$C_6$ alkyl, $C_3$–$C_6$ cycloalkyl, or a moiety of the formula (a), (b), or (c):

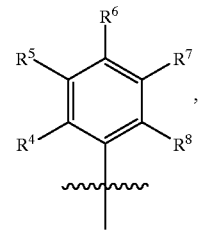

(a)

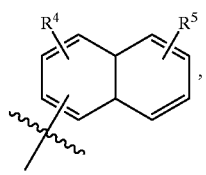

(b)

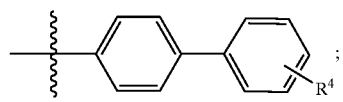

(c)

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy;

or a pharmaceutically acceptable salt or solvate thereof.

Further the current invention includes pharmaceutical formulations, comprising a compound of formula I(a), where —O—Pg is —O($C_1$–$C_4$ alkyl), —OCO($C_1$–$C_4$ alkyl), —OCOAr, —$OCO_2$($C_1$–$C_4$ alkyl), —$OCO_2$Ar, or $C_3$–$C_6$ cycloalkoxy, and pharmaceutically acceptable excipients.

DETAILED DESCRIPTION OF THE INVENTION

General chemical terms used in the description of compounds herein described bear their usual meanings. For example, "$C_1$–$C_4$ alkyl" refers to a methyl, ethyl, propyl, iso-propyl, n-butyl, s-butyl, or a t-butyl group. The term, "$C_1$–$C_6$ alkyl" would include the $C_1$–$C_4$ alkyl in addition to straight or branched aliphatic chains of 5 or 6 carbon atoms, e.g., pentyl, 2-methylbutyl, hexyl, 2-methylpentyl, 3-methylpentyl, and the like. The term "$C_1$–$C_4$ alkoxy" refers to a methoxy, ethoxy, propoxy, iso-propoxy, t-butoxy, s-butoxy, or a n-butoxy group. The term, "$C_3$–$C_6$ cycloalkyl" means a cyclopropyl, cyclobutyl, cyclopentyl, or a cyclohexyl group. The term "$C_3$–$C_6$ cycloalkoxy" refers to a cylclopropoxy, cyclobutoxy, cyclopentoxy or a cyclohexoxy group.

The symbol "Ar" refers to a phenyl or substituted phenyl group.

The term "substituted phenyl" refers to a phenyl group having one to three substituents selected from the group consisting of $C_1$–$C_4$ alkyl, $C_1$–$C_4$ alkoxy, hydroxy, nitro, chloro, fluoro, or tri(chloro or fluoro)methyl.

The term "halide" refers to chloro, bromo, or iodo.

The term "suitable solvent" refers to any solvent inert to the ongoing reaction that sufficiently solubilizes the reactants to effect the desired reaction.

The term "suitable kinetic base" refers to a strong base which provides a non-reversible deprotonation of an acidic substrate and is reactive enough to effect the desired reaction without significantly effecting any undesired reactions. Examples of kinetic bases include, but are not limited to, alkyl metals (e.g. n-butyl lithium, s-butyl lithium, and t-butyl lithium or ethyl magnesium bromide), metal amides such as lithium diisopropyl amide, metal alkoxides such as potassium t-butoxide, or metal hydrides (e.g. sodium, lithium, or potassium hydride).

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter "Greene".

Representative hydroxy protecting groups include, for example, $C_1$–$C_4$ alkyl ether groups, including methyl, ethyl, or isopropyl ether; substituted $C_1$–$C_4$ alkyl ether groups, including methoxymethyl ether, methylthiomethyl ether, tert-buylthiomethyl ether, (phenyldimethylsilyl) methoxymethyl ether, benzyloxymethyl ether, p-methoxy-benzyloxymethyl ether, and tert-butoxy-methyl ether; substituted ethyl ether groups such as ethoxyethyl ether, 1-(2-chloroethoxy)ethyl ether, 2,2,2-trichloroethoxymethyl ether, and 2-(trimethylsilyl)ethyl ether; and $C_3$–$C_6$ cycloalkyl ether groups, including cyclopentyl ether and cyclohexyl ether; phenyl and substituted phenyl ether groups such as phenyl ether, p-chlorophenyl ether, p-methoxyphenyl ether, and 2,4-dinitrophenyl ether; benzyl ether groups such as benzyl ether; and alkylsilyl ether groups such as trimethyl-triethyl- and triisopropylsilyl ethers, mixed alkylsilyl ether groups such as dimethylisopropylsilyl ether, and diethyliso-propylsilyl ether; and ester groups of the general formula $CO_2C_1$–$C_6$ alkyl or $CO_2Ar$, or specific esters such as formate ester, benzylformate ester, mono- di- and trichloroacetate esters, phenoxyacetate ester, and p-chlorophenoxyacetate, and the like. Acyl groups of the general formula $CO(C_1$–$C_6$ alkyl) or COAr and sulfonyl groups of the general formula $SO_2R^9$, where $R^9$ is Ar or $C_1$–$C_4$ alkyl, are also encompassed within the definition of hydroxy protecting group.

In general, the species of hydroxy protecting group employed is not critical so long as the derivatized hydroxy group is stable to the condition of subsequent reaction(s) on other positions of the intermediate molecule and can be selectively removed at the appropriate point without disrupting the remainder of the molecule including any other hydroxy protecting group(s). However, the skilled artisan will recognize that the definition of $R^a$, $R^{1a}$, and $R^{2a}$ in compounds of formula I(b) includes hydroxy protecting groups which form a subset of the hydroxy protecting groups listed above. Thus, to carry out the methods of the invention, the species of hydroxy group is important and only those groups embodied within the method claims are operative. For purposes of synthesizing compounds of formula I(a) or I(b), it is within the knowledge of one skilled in the art to select appropriate hydroxy protecting group(s) for a given set of reaction conditions given the guidance provided by Greene cited above.

The term "pharmaceutically acceptable salt" refers to base addition salts of compounds of formula I(a) or I(b) which are known to be non-toxic and are commonly used in the pharmaceutical literature. Commonly used basic addition salts would be the salts formed by: alkali or alkaline earth hydroxides, ammonium hydroxide, sodium hydroxide, alkyl or aromatic amines, and the like.

By "pharmaceutically acceptable" it is also meant that the carrier, diluent, excipients and salt must be compatible with the other ingredients of the formulation, in addition to, not being deleterious to the recipient thereof.

The term "solvate" represents an aggregate that comprises one or more molecules of the solute, such as a formula I(a) or I(b) compound, with one or more molecules of solvent.

As used herein, the term "effective amount" means an amount of a compound of formula I(b) which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

The term "inhibit" bears its usual meaning which includes prohibiting, ameliorating, halting, restraining, slowing or reversing the progression, or reducing the severity of hyper-lipidemia or a pathological symptom related to or resultant from hyperlipidemia, especially hypercholesterolemia. As such, these methods include both medical therapeutic (acute) and/or prophylactic (prevention) administration as appropriate.

SYNTHESIS

Compounds of formula I (a) which encompass all the compounds of formula I (b) except those where $R^3$ is a moiety of formula (a) wherein $R^4$, $R^5$, $R^6$, $R^7$, and $R^8$ are all hydrogen, may be synthesized by the routes illustrated in Scheme 1 and 2 below. Compounds of formula I(b), where $R^3$ is a moiety of formula (a) where $R^4$, $R^5$, $R^6$, $R^7$, and $R^8$ are all hydrogen, can be prepared by analogy to the methods discussed in Schemes 1 and 2 below. In Schemes 1 and/or 2, Halo, R, $R^1$, $R^2$, $R^{3a}$ are as described supra.

INDENES AND DIHYDRONAPTHALENES

The compounds of formula I(a) where x is —$CH_2$— (indenes) or —$CH_2CH_2$— (dihydronapthalenes) may be synthesized by the route illustrated in Scheme 1 where n is 1 or 2.

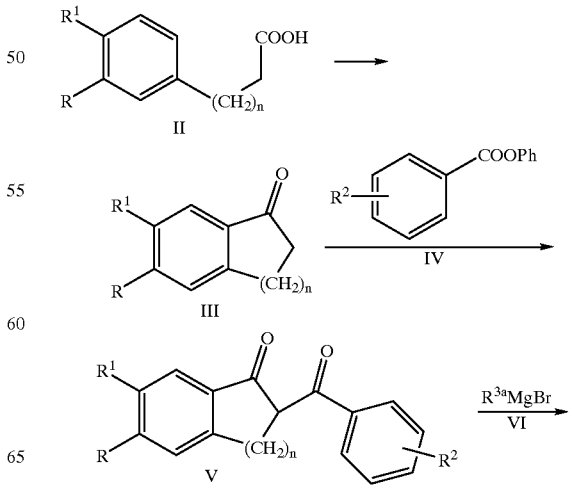

SCHEME 1

-continued

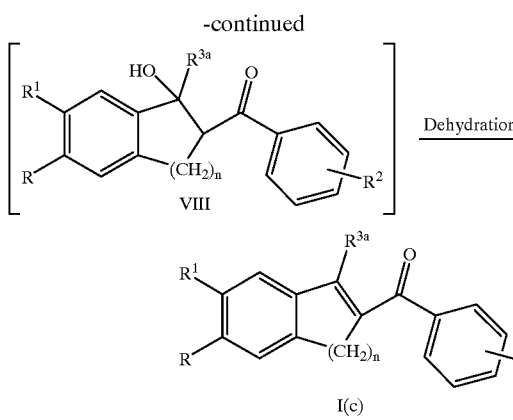

The first step in the synthetic sequence is the cyclization of an appropriately substituted phenylpropionic acid or phenylbutyric acid of formula II in the presence of a strong dehydrating acid, e.g., polyphosphoric acid, concentrated sulfuric acid, and the like. Such reactions are usually carried out at elevated temperatures using either the acid e.g., polyphosphoric acid, or a high boiling, inert liquid as a solvent, e.g., chlorobenzene, toluene, and the like. Such reactions are usually complete in two to twenty hours when conducted at temperatures above 100° C. This step yields the indanones (n=1) and tetralones (n=2) of formula III.

The compounds of formula III may be converted to the diketones of formula V by installation of a benzoyl moiety onto a compound of formula III. This conversion is accomplished by dissolving or suspending a compound of formula III in a suitable solvent and adding a suitable kinetic base to form the corresponding anion. A preferred kinetic base is typically an alkaline metal amide such as lithium amide. Suitable solvents include, but are not limited to tetrahydrofuran, ether, hexane, methylene chloride, mixtures thereof, and the like. Tetrahydrofuran is typically the preferred solvent. The deprotonation is generally run at temperatures from ambient to −50° C., preferably at 0° C. Once the anion is formed, typically in about ten minutes at 0° C., a compound of formula IV may be added directly to the cold anion solution to yield, after stirring at ambient temperature for about 2 hours, a diketone of formula V.

Compounds of formula I(c) may be prepared from a commercially available Grignard reagent of formula VI and a compound of formula V. The Grignard reagent may alternatively be made by dissolving a commercially available compound of the formula $R^3$-Halide in the presence of magnesium and mercury (II) chloride in a mutually inert solvent. Once the Grignard reagent is formed, a diketone of formula V may be added to provide the intermediate alcohol of formula VII. Of the standard Grignard reagents known in the art, the magnesium bromide would be preferred. The compound of formula VI is generally employed in a substantial molar excess, for example in from a three molar excess to about a ten molar excess relative to the compound of formula V, preferably in about a 5 molar excess. Typical solvents suitable for use in this reaction include tetrahydrofuran but diethyl ether is preferred. The reaction is generally substantially complete after about 1 to 24 hours when conducted at a temperature in the range of from about ambient to the reflux temperature of the reaction mixture. The reaction is preferably conducted under controlled reflux conditions for about 2 to 6 hours. The alcohol of formula VII is typically dehydrated under the conditions of its formation described above to yield the compound of formula I(c).

NAPHTHALENES

The compounds of formula I(a) where X is —$CH_2$=$CH_2$— (naphthalenes) may be prepared by oxidation of dihydronaphthalene derivatives of formula I(d), as illustrated in Scheme 2 below.

SCHEME 2

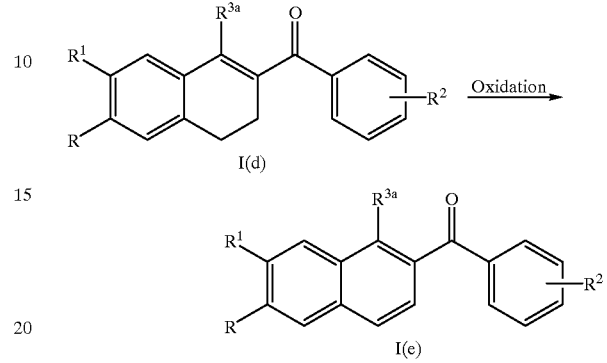

Compounds of formula I(e) may be prepared by dissolving or suspending a compound of formula I(d) (i.e. a compound of formula I(c) where n is 2) in a suitable solvent and adding an oxidant. Choices of oxidants and solvents may be found in Larock, *Comprehensive Organic Transformations*, VCH Publishers, Inc., New York, N.Y., 1989, pg. 95. A preferred oxidant is 2,3-dichloro-5,6-dicyano-1,4-benzoquinone (DDQ). Benzene or toluene is the preferred solvent. While the amount of oxidant employed will vary with the particular oxidant, when DDQ is the oxidant, it is employed in a molar excess. For example, a 1.2 to a 1.6 molar excess, relative to the compound of formula I(d), is usually employed. A 1.3 molar excess is typically preferred. This reaction is most often run at temperatures between 25° C. and 125° C. and is preferably run at about 80° C. Under these conditions, the reaction is usually completed in one to twenty hours.

When any of R, $R^a$, $R^1$, $R^{1a}$, $R^2$, or $R^{2a}$ are hydroxy protecting groups in compounds of formula I(a) or I(b), they may be removed by well known methods in the art. Numerous reactions for the formation and removal of the hydroxy protecting groups contemplated within the scope of this invention are described in a number of standard works including, for example in *The Peptides*, Vol. I, Schrooder and Lubke, Academic Press (London and New York, 1965) or in Greene. Methods for removing preferred hydroxy protecting groups, particularly methyl groups, are essentially as described in Example 2 infra. In addition, if compounds of formula I(a) contain a hydroxy protecting group(s) which is not operative in the methods of the current invention, it may be removed and an operative hydroxy protecting group(s) may be installed as described in Greene or as described in the paragraph below.

Compounds of formula I(a) or I(b), where R, $R^a$, $R^1$, $R^{1a}$, $R^2$, or $R^{2a}$ are acyl derivatives of the free phenols, may be obtained by removal of the non-acyl hydroxy protecting groups when present and acylation with the appropriate acylating agent. Compounds of formula I(a), where R, $R^1$, and $R^2$ are sulfonyl derivatives of the free phenols, may be obtained by removal of the non-sulfonyl hydroxy protecting groups when present and sulfonation with the appropriate sulfonating agent. Methods for the acylation or sulfonation of the deprotected compounds is essentially revealed in U.S. Pat. No. 4,358,593, the teachings of which are herein incorporated by reference.

For specific instruction on the synthesis of compounds of formula I(b) where $R^3$ is phenyl see U.S. Pat. No. 4,075,227 the teaching of which are hereby incorporated by reference.

The optimal time for performing the reactions of Schemes 1 and 2 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. Intermediate and final products may be purified, if desired by common techniques such as recrystallization or chromatography over solid supports such as silica gel or alumina.

Compounds of formula III, IV, and VI are either commercially available or may be prepared by methods well known in the art.

Application of the above chemistry enables the synthesis of the compounds of formula I(a), which include, but is not limited to:

2-(4-hydroxybenzoyl)-3-(3-chlorophenyl)-6-hydroxyindene;

2-(4-hydroxybenzoyl)-3-(2-methyl-4-methoxyphenyl)-5-hydroxyindene;

2-(4-methoxybenzoyl)-3-(4-fluorophenyl)-6-hydroxyindene;

2-(4-hydroxybenzoyl)-3-(2,3-difluorophenyl)-6-methoxyindene;

2-(4-methoxybenzoyl)-3-(2,5-dimethylphenyl)-6-methoxyindene;

2-(4-cyclopentyloxybenzoyl)-3-(4-methylphenyl)-6-hydroxyindene;

2-(4-cyclopentylxybenzoyl)-3-(3-chlorophenyl)-5-hydroxyindene;

2-(4-hydroxybenzoyl)-3-(4-phenylphenyl)-6-hydroxyindene;

2-(4-hydroxybenzoyl)-3-(3-methylphenyl)-6-hydroxyindene;

2-(4-hydroxybenzoyl)-3-(4-methylphenyl)-5-hydroxyindene;

2-(4-hydroxybenzoyl)-3-ethyl-6-hydroxyindene;

2-(4-hydroxybenzoyl)-3-cyclohexyl-6-hydroxyindene;

2-(4-benzoyloxybenzoyl)-3-isopropyl-5-hydroxyindene;

2-(4-methoxybenzoyl)-3-pentyl-5-hydroxyindene;

2-(4-hydroxybenzoyl)-3-(4-ethoxyphenyl)-5,6-dihydroxyindene;

2-(4-hydroxybenzoyl)-3-(2,4-dichlorophenyl)-5-methoxy-6-hydroxyindene;

1-phenyl-2-(4-hydroxybenzoyl)-3,4-dihydro-6-hydroxynaphthalene;

1-(2-isopropoxyphenyl)-2-(4-methoxybenzoyl)-3,4-dihydro-6-methoxynaphthalene;

1-(4-chlorophenyl)-2-(4-hydroxybenzoyl)-3,4-dihydro-7-hydroxynaphthalene;

1-(4-methylphenyl)-2-(4-hydroxybenzoyl)-3,4-dihydro-6-hydroxynaphthalene;

1-(2-hydroxyphenyl)-2-(4-acetyloxybenzoyl)-3,4-dihydro-6-hydroxynaphthalene;

1-methyl-2-(4-hydroxybenzoyl)-3,4-dihydro-6-hydroxynaphthalene;

1-cyclohexyl-2-(4-hydroxybenzoyl)-3,4-dihydro-7-hydroxynaphthalene;

1-phenyl-2-(4-cyclohexyloxybenzoyl)-3,4-dihydro-6-hydroxynaphthalene;

1-phenyl-2-(4-benzoyloxybenzoyl)-3,4-dihydro-6-benzoyloxynaphthalene;

1-phenyl-2-(4-hydroxybenzoyl)-3,4-dihydronaphthalene 1-(2,4-difluorophenyl)-2-(3-hydroxybenzoyl)-3,4-dihydro-6,7-dihydroxynaphthalene;

1-(2,5-dihydroxyphenyl)-2-(4-hydroxybenzoyl)-6-hydroxynaphthalene;

1-(2,4,6-trimethylphenyl)-2-(4-hydroxybenzoyl)-7-hydroxynaphthalene;

1-(4-methylphenyl)-2-(3-hydroxybenzoyl)-6-hydroxynaphthalene;

1-methyl-2-(4-hydroxybenzoyl)-6-hydroxynaphthalene;

1-(2,3,4,5,6-pentafluorophenyl)-2-(4-acetyloxybenzoyl)-6-hydroxynaphthalene;

1-(4-hydroxyphenyl)-2-(4-hydroxybenzoyl)-6,7-dihydroxynaphthalene;

1-(2,3,4-trimethylphenyl)-2-(4-hydroxybenzoyl)-6-methoxynaphthalene;

1-(4-chlorophenyl)-2-(4-methoxybenzoyl)-6-hydroxynaphthalene;

1-(4-methylphenyl)-2-(4-hydroxybenzoyl)-6-hydroxynaphthalene;

1-ethyl-2-(4-hydroxybenzoyl)-6-hydroxynaphthalene;

1-isopropyl-2-(4-hydroxybenzoyl)-6-hydroxynaphthalene;

1-(3-methylphenyl)-2-(4-hydroxybenzoyl)-6-hydroxynaphthalene;

1-methyl-2-(4-cyclopentyloxybenzoyl)-6-hydroxynaphthalene; and the like.

The following examples are provided for the purpose of illustrating the preparation of the compounds of the current invention and are not intended to limit its scope.

In the following Preparations and Examples, the terms melting point, proton nuclear magnetic resonance spectra, electron impact mass spectra, elemental analysis, high performance liquid chromatography, and thin layer chromatography are abbreviated "mp", "$^1$H NMR", "MS(EI)", "EA", "HPLC", and "TLC", respectively. The values reported for MS(EI) correspond to mass numbers unless otherwise indicated.

Preparations

Preparation 1

1-Oxo-5-Methoxyindane

A mixture of 5 g of 3-(3-methoxyphenyl)propionic acid in polyphosphoric acid was prepared. The mixture was heated for 2 hours at 120° C. The mixture was cooled and ice was added. The resulting solid was removed by filtration and dissolved in benzene. The benzene solution was filtered and concentrated to one-fourth its original volume. Petroleum ether was added and the mixture was cooled to 5° C. The product was collected by filtration.

mp: 105° C.–107° C. EA: Calc. for $C_{10}H_{10}O_2$: C, 74.06; H, 6.22; O, 19.73. Found: C, 74.32; H, 6.42; O, 20.03.

Preparation 2

1-Oxo-2-(4-Methoxybenzoyl)-5-Methoxyindane

A solution of 22.2 g (137 mmol) of 1-oxo-5-methoxyindane in tetrahydrofuran was added dropwise to a cold suspension of 11 g (274 mmol) of sodium amide in tetrahydrofuran. The resulting mixture was stirred for ten minutes and a solution of 31.3 g (137 mmol) of phenyl-4-methoxybenzoate in tetrahydrofuran was added. Cooling was discontinued and a slight exothermic reaction occurred. The mixture was stirred at ambient temperature for an additional two hours. A thick precipitate developed and the reaction mixture was poured into ice-water. The aqueous mixture was extracted with ethyl acetate. The ethyl acetate extract was evaporated to dryness to obtain 20.7 g of the title compound. mp: 160° C.–162° C.

Preparation 3

2-(4-Methoxybenzoyl)-6-Methoxy-a-Tetralone

To a suspension of 10.5 g of sodium amide in tetrahydrofuran was added 23.2 g of 6-methoxy-a-tetralone in tetrahydrofuran. The resulting mixture was stirred for ten minutes and a solution of 30 g of phenyl 4-methoxybenzoate in tetrahydrofuran was added. The reaction was allowed to proceed for sixteen hours at ambient temperature. The reaction was concentrated in vacuo and water was added to the residue. The mixture was filtered and the residue slurried in hot methanol. The hot methanol was allowed to cool and 24.3 g of the title compound crystallized out.

mp: 112° C.–113° C. EA: Calc. for $C_{19}H_{18}O_3$: C, 75.53; H, 5.85; O, 20.62. Found: C, 72.23; H, 6.55, O, 20.67. MS(EI): 310 (M+).

EXAMPLES

EXAMPLE 1

2-(4-Methoxybenzoyl)-3-Phenyl-6-Methoxyindene

A slurry of 20.5 g (97 mmol) of 1-oxo-2-(4-methoxybenzoyl)-5-methoxyindane in benzene was added as a slow stream to a solution of a five-fold excess of phenylmagnesium bromide in ether. The resulting mixture was heated to reflux for four hours, cooled, and poured into a mixture of ice-sulfuric acid. The mixture was extracted with ethyl acetate. The ethyl acetate extract was washed with water, then with aqueous sodium bicarbonate solution, and dried over magnesium sulfate. After filtering, the mixture was concentrated to 28 g of a dark red oil. A mixture of 20% ether in methanol (25 mL) was added. Part of the oil crystallized on standing at ambient temperature and was isolated by filtration to obtain 7.5 g of red crystals. This material was slurried in a hot mixture of benzene and acetone. The insoluble solid was separated by filtration. The filtrate was concentrated to dryness and the residue was crystallized from ether to obtain 5.4 g of the title compound. The filtrate from the aforementioned separation of the red crystals was concentrated and chromatographed on a silica gel column eluted with benzene. From the chromatography was obtained an additional 3 g of the title compound. These two portions of the product were combined and recrystallized from acetone to yield the final form of the title compound.

mp: 115–116° C. EA: Calc. for $C_{24}H_{20}O_3$: C, 80.88; H, 5.66; O, 13.47. Found: C, 80.95; H, 5.84; O, 14.42.

EXAMPLE 2

2-(4-Methoxybenzoyl)-3-Phenylindene

A slurry of 13.25 g (50 mmol) of 1-oxo-2-(4-methoxybenzoyl)indane in a mixture of 300 mL of ether and 300 mL of benzene was prepared. To the slurry was added 35.66 g (197 mmol) of phenylmagnesium bromide. The resulting mixture was heated to reflux for sixteen hours and poured into a mixture of ice and sulfuric acid. The mixture was allowed to separate and the organic layer was removed. The organic extract was washed with a bicarbonate solution, dried over sodium sulfate, filtered, and concentrated to a red oil. A small amount of ether was added to the oil and a crystalline precipitate formed. The crystals were removed by filtration. The filtrate was concentrated to dryness and the product crystallized from methanol to yield 9.3 g of the title compound.

mp: 114° C.–115° C. EA: Calc. for $C_{23}H_{18}O_2$: C, 84.64; H, 5.56; O, 9.80. Found: C, 84.69; H, 5.82; O, 9.79.

EXAMPLE 3

2-(4-Hydroxybenzoyl)-3-Phenyl-6-Hydroxyindene

To a solution of 4 g of 2-(4-methoxybenzoyl)-3-phenyl-6-methoxyindene in methylene chloride was added two equivalents of boron tribromide. The resulting mixture was stirred for twenty four hours at ambient temperature. Monitoring of the reaction by TLC indicated a small amount of mono-methoxy compound present, therefore, an additional equivalent of boron tribromide was added and the reaction was allowed to proceed for seventy-two hours. The reaction was concentrated to dryness and chromatographed on a silica gel column eluted with a solvent mixture of benzene-:ethyl acetate (9:1)(v/v). This yielded 3 g of the title compound.

mp: 191° C.–192° C. EA: Calc. for $C_{22}H_{16}O_3$: C, 80.47; H, 4.91; O, 14.62. Found: C, 80.28; H, 4.98; O, 14.71.

EXAMPLE 4

1-Phenyl-2-(4-Methoxybenzoyl)-3,4-Dihydro-6-Methoxynaphthalene

To 500 mL of a 1:1 mixture of ether and benzene was added 21.7 g (70 mmol) of 2-(4-methoxybenzoyl)-6-methoxy-a-tetralone. To this slurry was added 146 mL of 2.05 molar solution (300 mmol) of phenylmagnesium bromide in ether. The green reaction mixture was heated to reflux for four hours and then poured into a mixture of ice/sulfuric acid. The slurry was extracted with ethyl acetate. The ethyl acetate extract was washed with water, bicarbonate solution, then again with water, and finally dried over magnesium sulfate. The extract was filtered then evaporated to a red-yellow oil. The product oil was crystallized from ether to yield 13.8 g of the title compound as a white solid.

mp: 107° C.–108° C. EA: Calc. for $C_{25}H_{22}O_3$: C, 81.06; H, 5.99; O, 12.96. Found: C, 81.14; H, 5.79; O, 12.93. MS(EI): 370 (M+).

EXAMPLE 5

1-Phenyl-2-(4-Hydroxybenzoyl)-3,4-Dihydro-6-Hydroxynaphthalene

To a cold 300 mL of dimethylformamide and under a nitrogen atmosphere was added 9.3 g of ethylmercaptan. To this mixture was added 7.2 g of 50% sodium hydride (150 mmol) in oil. To this mixture was added 11.1 g (30 mmol) of 1-phenyl-2-(4-methoxybenzoyl)-3,4-dihydro-6-methoxynaphthalene and the reaction mixture was heated to 60° C. for two hours. The reaction was acidified with the addition of 1N hydrochloric acid and extracted with ethyl acetate. The ethyl acetate extract was washed with water and evaporated to dryness. The final product was crystallized from a mixture of methanol-acetone to yield 8 g of the title compound.

mp: 205° C.–207° C. EA: Calc. for $C_{23}H_{18}O_3$: C, 80.68; H, 5.30; O, 14.02. Found: C, 80.38; H, 5.43; O, 14.28.

EXAMPLE 6

1-Phenyl-2-(4-Methoxybenzoyl)-6-Methoxynaphthalene

To 11.1 g (30 mmol) of 1-phenyl-2-(4-methoxybenzoyl)-3,4-dihydro-6-methoxynaphthalene dissolved in benzene was added DDQ (9 g, 40 mmol). The mixture was heated to reflux for two hours and filtered while hot through silica gel. The silica gel was washed three times with ethyl acetate. The ethyl acetate washings and the benzene solution were combined and evaporated to dryness. The residue was crystallized from hot methanol, which yielded 4.5 g of the title compound.

mp: 122° C.–124° C. EA: Calc. for $C_{25}H_{18}O_3$: C, 80.86; H, 5.30; O, 14.02. Found: C, 80.83; H, 5.68; O, 12.93. MS(EI): 368 (M+).

The following examples demonstrating the methods of the current invention are given for the purpose of illustration and are not meant to be limiting in any way.

Assay 1

Seventy-five day old female Sprague Dawley rats (weight range of 200 g to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

A representative compound of the current invention, when assayed by this method, gave the positive results reported in Table 1 below.

TABLE 1

| Compound | Serum Cholesterol (% decrease vs Control) |
| --- | --- |
| 1-phenyl-2-(4-methoxybenzoyl)-6-methoxynaphthalene (Compound of Example 6) | 75.3* @ 0.1[a] <br> 71* @ 1.0[a] <br> 53.3* @ 10.0[a] |
| 17a-ethynylestradiol | 78.4* @ 0.1[a] |

[a]Dose in mg/kg P.O.
*$p < 0.05$

Assay 2

Forty-one to forty-three day old Sprague Dawley male rats (weight range 200 g to 225 g) were obtained from Harlan (Indianapolis, Ind.). Upon arrival, the animals were housed in metal hanging cages with 6 or 7 animals per cage, with access to food and water, ad libitum. After one or two days, the animals were housed individually, ambient temperature was maintained at 22.2° C. with a relative humidity of 40%. The photoperiod in the room was 12 hours of dark and 12 hours of light.

Dosing Regimen Tissue Collection. After a one week acclimation period daily dosing with the test compounds or standards was initiated. The animals were weighed after two days of dosing and the doses were adjusted for any change in the animals weight. All compounds were given by oral gavage in a formulation of 0.5 mL of 1% aqueous carboxymethylcellulose. The animals were dosed for four days. At the end of the dosing period, the animals were weighed and rendered unconscious with carbon dioxide. Blood samples were collected by cardiac puncture into EDTA treated tubes and a portion of the liver was removed and rapidly frozen Liver portions were stored at −80° C. in liquid nitrogen for further analysis.

Lipid Analysis. Plasma was obtained by centrifugation of the blood sample for 10 minutes at 2500 rpm. Plasma cholesterol was determined using a WAKO Diagnostic Cholesterol II Assay.

Hepatic Lipase Assay. A portion of the liver was homogenized in normal saline containing 20 units of heparin per mL. After a 30 minute incubation at ambient temperature, the homogenate was centrifuged for 3 minutes at 8000 g, and the supernatant collected for assay. Hepatic lipase activity was determined essentially by the method of Henderson et al., using $H^3$ triolein in an acacia emulsion as a substrate. Free fatty acids were separated from non-hydrolyzed substrate by the addition of fumed silica according to Borensztajn et al. and quantitated by liquid scintillation. (See: Henderson, A. D., Richmond, W., and Elkeles, R. S., "Hepatic and Lipoprotein Lipases Selectively Assayed in Postheparin Plasma.", Clin. Chem., 39/2, p. 218–223 (1993). Borensztajn, J., Reddy, M. N., and Gladstone, A. R., "A Simple Method for the Separation of Triacylglycerols from Fatty Acids Released in Lipase Assays.", J. Lipdid Res., 29, p. 1549–1552 (1988).)

Positive results using representative compounds of the current invention demonstrate the potential for the methods of the current invention.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical formulation comprising an effective amount of a compound of formula I(a), where R, $R^1$, and $R^2$ are independently at each occurrence hydrogen, hydroxy, $-O(C_1-C_4$ alkyl), $-OCO(C_1-C_4$ alkyl), $-OCOAr$, $-OCO_2$ ($C_1-C_4$ alkyl), $-OCO_2Ar$, or $C_3-C_6$ cycloalkoxy; or a pharmaceutically acceptable salt thereof, (hereafter referred to as compounds of formula I(f)) and a pharmaceutical carrier, diluent, or excipient.

The total active ingredients in such formulations comprises from 0.1% to 99.9% by weight of the formulation. A typical daily dose will contain a nontoxic dosage level of from about 1 mg to about 600 mg/day of a compound of formula I(f) or I(b). Preferred daily doses generally will be from about 5 mg to about 80 mg/day.

Pharmaceutical formulations of the present invention can be prepared by procedures known in the art using well known and readily available ingredients. For example, the compounds of formula I(f) can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

Compounds of formula I(f) also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I(b) and I(f), generally, will be administered in a convenient formulation as determined by the attending physician. The following formulation examples are only illustrative and are not intended to limit the scope of the present invention.

Formulations

In the formulations which follow, "active ingredient" means a compound of formula I(f), or a pharmaceutically acceptable salt or solvate thereof.

Hard gelatin capsules are prepared using the following:

| Formulation 1 Gelatin Capsules | |
|---|---|
| Ingredient | Quantity (mg/capsule) |
| Active ingredient | 0.1–1000 |
| Starch, NF | 0–650 |

| -continued | |
|---|---|
| Formulation 1 Gelatin Capsules | |
| Ingredient | Quantity (mg/capsule) |
| Starch flowable powder | 0–650 |
| Silicone fluid 350 centistokes | 0–15 |

The formulation above may be changed in compliance with the reasonable variations provided.

A tablet formulation is prepared using the ingredients below:

| Formulation 2 Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

| Formulation 3 Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C.–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

| Formulation 4 Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |

-continued

| Formulation 4 Suspensions | |
| --- | --- |
| Ingredient | Quantity (mg/5 ml) |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5 Aerosol | |
| --- | --- |
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6 Suppositories | |
| --- | --- |
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7 Intravenous Solution | |
| --- | --- |
| Ingredient | Quantity |
| Active ingedient | 50 mg |
| Isotonic saline | 1,000 mL |

The solution of the above ingredients is intravenously administered to a patient at a rate of about 1 ml per minute.

What is claimed is:

1. A method of inhibiting hyperlipidemia comprising administering to a mammal in need thereof an effective amount of a compound of formula I(b):

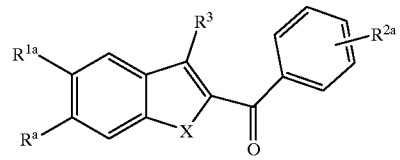

I(b)

where $R^a$, $R^{1a}$, and $R^{2a}$ are independently at each occurrence hydrogen, hydroxy, —O($C_1$–$C_4$ alkyl), —OCO($C_1$–$C_4$ alkyl), —OCOAr, —OCO$_2$($C_1$–$C_4$ alkyl), —OCO$_2$Ar, or $C_3$–$C_6$ cycloalkoxy;

Ar is phenyl or substituted phenyl;

X is —CH$_2$—, —CH$_2$—CH$_2$—, or —CH═CH—;

$R^3$ is hydrogen, $C_1$–$C_6$ alkyl, $C_3$–$C_6$ cycloalkyl, or a moiety of the formula (a), (b), or (c):

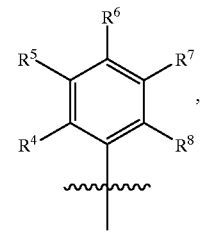

(a)

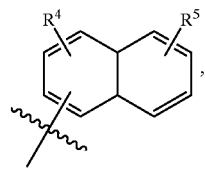

(b)

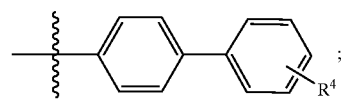

(c)

wherein $R^4$, $R^5$, $R^6$, $R^7$, and $R^8$ are independently at each occurrence hydrogen, fluoro, chloro, bromo, $C_1$–$C_4$ alkyl, $C_3$–$C_6$ cycloalkyl, or $C_1$–$C_4$ alkoxy;

or a pharmaceutically acceptable salt or solvate thereof.

2. A method according to claim 1 wherein said mammal is a human.

3. A method according to claim 2 wherein said human is female.

4. A method according to claim 3 wherein said female is post-menopausal.

5. A method according to either claim 2 or claim 3 wherein the hyperlipidemia is hypercholesterolemia.

6. A method according to either claim 2 or claim 3 wherein the hyperlipidemia results in atherosclerosis.

7. A method according to claim 2 wherein said compound of formula I(b) is a compound wherein $R^{2a}$ is not hydrogen and $R^{1a}$ is hydrogen.

8. A method according to claim 7 wherein said compound of formula I(b) is a compound wherein $R^3$ is a moiety of formula (a) and $R^4$, $R^5$, $R^6$, $R^7$, and $R^8$ are all hydrogen.

9. A method according to claim 8 wherein $R^a$ and $R^{2a}$ are both methoxy.

10. A method according to claim 8 wherein $R^a$ and $R^{2a}$ are both hydroxy.

11. A method according to claim 2 wherein said compound of formula I(b) is 1-phenyl-2-(4-methoxybenzoyl)-6-methoxynaphthalene.

* * * * *